US011541225B2

(12) United States Patent
Najar

(10) Patent No.: US 11,541,225 B2
(45) Date of Patent: Jan. 3, 2023

(54) VASCULAR COUPLING DEVICE

(71) Applicant: SCANDINAVIAN REAL HEART AB, Västerås (SE)

(72) Inventor: Azad Najar, Västerå s (SE)

(73) Assignee: SCANDINAVIAN REAL HEART AB, Västerås (SE)

(*) Notice: Subject to any disclaimer, the term of this patent is extended or adjusted under 35 U.S.C. 154(b) by 0 days.

(21) Appl. No.: 17/049,248

(22) PCT Filed: Apr. 25, 2019

(86) PCT No.: PCT/EP2019/060687
§ 371 (c)(1),
(2) Date: Oct. 20, 2020

(87) PCT Pub. No.: WO2019/207076
PCT Pub. Date: Oct. 31, 2019

(65) Prior Publication Data
US 2021/0244939 A1 Aug. 12, 2021

(30) Foreign Application Priority Data
Apr. 25, 2018 (SE) ..................... 1850498-5

(51) Int. Cl.
A61M 60/859 (2021.01)
A61M 60/148 (2021.01)
(Continued)

(52) U.S. Cl.
CPC ........ A61M 60/859 (2021.01); A61M 60/148 (2021.01); A61M 60/178 (2021.01);
(Continued)

(58) Field of Classification Search
CPC .............. A61M 60/122; A61M 60/857; A61M 2205/17; A61M 2205/8206;
(Continued)

(56) References Cited

U.S. PATENT DOCUMENTS

| 8,535,213 B2 | 9/2013 | Min et al. |
| 9,314,559 B2 | 4/2016 | Smith et al. |
| 2009/0204206 A1 | 8/2009 | Parquet et al. |

FOREIGN PATENT DOCUMENTS

WO 2016020219 2/2016

OTHER PUBLICATIONS

International Search Report and Written Opinion for corresponding International Application No. PCT/EP2019/060687 dated Jul. 15, 2019.

Primary Examiner — Jon Eric C Morales
(74) Attorney, Agent, or Firm — Renner, Otto, Boisselle & Sklar, LLP

(57) ABSTRACT

A vascular coupling device for connecting an artificial heart pump to the vascular system of a subject is disclosed. The artificial heart pump may form part of a total artificial heart (TAH). The vascular coupling device comprises a first and a second coupling element, each one of said first and second coupling elements has a first end comprising a resilient coupling portion, a second end comprising a vascular grafting material, and a tubular midsection is arranged between said first and second ends. The vascular coupling device further comprises a coupling plate comprising a first receptor and a second receptor configured and adapted for receiving said resilient coupling portions of the first and second coupling elements. The vascular coupling device further comprises a docking plate, comprising a first and a second docking port configured to be arranged to an inlet channel and an outlet channel of said artificial heart pump and one or more fastening means for connecting said coupling plate to the docking plate. A method for connecting the vascular coupling device to the vascular system of a subject is also disclosed.

15 Claims, 8 Drawing Sheets

(51) Int. Cl.
    *A61M 60/861* (2021.01)
    *A61M 60/196* (2021.01)
    *A61M 60/178* (2021.01)
    *A61M 60/205* (2021.01)
(52) U.S. Cl.
    CPC ........ *A61M 60/196* (2021.01); *A61M 60/205* (2021.01); *A61M 60/861* (2021.01)
(58) Field of Classification Search
    CPC .......... A61M 2205/8243; A61M 5/148; A61M 60/00; A61M 60/148; A61M 60/205; A61M 60/268; A61M 60/40; A61M 60/422; A61M 60/50; A61M 60/818; A61M 60/894
    See application file for complete search history.

VASCULAR COUPLING DEVICE

This application is a national phase of International Application No. PCT/EP2019/060687 filed Apr. 25, 2019 and published in the English language, which claims priority to Swedish Application 1850498-5, filed Apr. 25, 2018 both of which are hereby incorporated herein by reference.

TECHNICAL FIELD

The present invention relates to a vascular coupling device for connecting a total artificial heart (TAH) to the vascular system of a subject in need of a total artificial heart.

BACKGROUND OF THE INVENTION

The main function of the heart in the human body is to circulate blood through the blood vessels in order to transport oxygen, nutrition, and waste products to and from body cells. Many diseases may affect the heart such as myocardial infarction, hypertension, valve insufficiency and various heart muscle diseases. The end result of such diseases may be heart failure which means that the heart has lost its ability to pump enough blood to the lungs and body tissues.

The symptoms of heart failure are shortness of breath, edema and fatigue. The only treatment option available for a patient suffering from advanced heart failure is heart transplantation. However, due to a lack of sufficient number of donor hearts the majority of advanced heart failure patients die while waiting for a heart transplant operation.

For this reason many efforts have been made during the last 50 years to develop a mechanical heart which can replace a diseased heart entirely. Until now only a few Total Artificial Hearts (TAH) i.e. mechanical hearts/heart prosthesis have been developed which have the capacity to completely replace the diseased heart.

WO2016/020219 discloses a four-chambered TAH which is designed as a human heart. This TAH comprises a first and a second artificial heart pump corresponding to the left and right heart of the natural heart. Each artificial pump comprises an inlet and an outlet channel and a valve cylinder which is divided into two chambers by means of a moving plane comprising a one-way valve which corresponds to the atrioventricular (AV) plane in a natural heart. Pump actuating means are configured to apply a movement to said valve cylinders in an upward and downward direction in response to control signals from a control unit such that when the valve cylinders move in an upward direction inside the blood pump housing device, the valves provided in the valve planes are in an open position allowing a flow of blood through the inlet channel into the artificial atrium, and thereafter into the artificial ventricle. When the valve cylinders move in a downward direction the valves are in the closed position and blood is ejected from the artificial ventricle and exit therefrom through outlet channels.

The TAH is enclosed in a casing which protects the surrounding tissue from moving parts and prevents entry of body fluids into the TAH. When implanted in a subject the diseased natural heart of the subject is removed and thereafter the circulatory system of the subject is connected to the inlets and outlets of the TAH. The coupling device connecting the vascular system with the inlets and outlets of the TAH has to be absolutely leak-proof as well as easy to connect and disconnect from the TAH. Furthermore, the vascular coupling device must have the capacity to elastically accommodate any body movements of the subject without damaging the vascular system of the patient, or disconnecting it from the TAH.

SUMMARY OF THE INVENTION

The vascular coupling device as disclosed herein will provide an absolutely leak-proof connection between the vascular system of the patient and the inlets and outlets of an artificial heart pump. In cases when the patient requires a TAH, the vascular system of the patient will be connected to two artificial heart pumps. The vascular coupling device is easily connected to the circulatory system of the subject, i.e. both the systemic circuit and the pulmonary circuit as well as to artificial heart pumps in a leak-proof and flexible manner.

In some situations the subject requires only one artificial heart pump, e.g. when the artificial heart pump is used as a Left Ventricular Assist Device (LVAD) or a Right Ventricular Assist Device (RVAD). The vascular coupling device may also be used when connecting a subject's vascular system to a TAH. In these situations two vascular coupling devices are required to connect to the two artificial heat pumps of a TAH.

The vascular coupling device as disclosed herein comprises a first and a second coupling element. The first and second coupling elements have a tubular conformation. Each one of said first and second coupling elements has a first end comprising a resilient coupling portion and a second end comprising a vascular grafting material. A tubular midsection is arranged between the first and second ends, connecting the vascular grafting material to the resilient coupling portion.

The vascular coupling device further comprises a coupling plate comprising a first receptor and a second receptor. The first and second receptors are configured and adapted for receiving the resilient coupling portions of the first and second coupling elements.

The vascular coupling device further comprises a docking plate comprising a first and a second docking port. The first and second docking ports are configured to be arranged to an inlet channel and an outlet channel of the artificial heart pump.

The vascular coupling device also comprises one or more fastening means for connecting said coupling plate to the docking plate.

The first end of said first and second coupling elements comprises a resilient coupling portion made from a resilient material. The resilient docking portion must be bio-compatible and blood compatible and may be chosen from a resilient material of the group consisting of polyethylene, polyamide, polymethylmethacrylate, polytetrafluroethylene, polyurethane, and silicones such as dimethyl siloxane, polydimethylsiloxane, and decamethyl cyclopentasiloxane, or combinations thereof.

The resilient coupling portions have a tubular configuration with an open end forming an orifice. The open end may have any geometric outline such as circular, oval, quadratic or rectangular. In one advantageous embodiment the open end has a circular outline. The outer circumference of the open end is provided with collars having an outwardly folded rim.

The second end of the first and second coupling elements is provided with a vascular grafting material. Said vascular grafting material must be blood-compatible and may be chosen from any known commercially available vascular grafting materials such as e.g. polyethylene teraphthalate (Dacron), expanded polytetrafluoroethylene (ePTFE), Polyamide (nylon) and polyurethane. In one embodiment the vascular grafting material is polyethylene teraphthalate (Dacron). The blood vessels from the circulatory system of the subject (i.e. both from the pulmonary and the systemic circuits) are grafted to the vascular grafting material of the second ends of the first and second coupling elements.

A tubular midsection connects the first ends and the second ends of the first coupling elements. The tubular midsection is advantageously made from the same material as the vascular grafting material. The tubular connecting portion may have different shapes depending on whether the vascular coupling device is connected to the first or the second artificial heat pump. The tubular midsection is normally straight but may have the shape of a tube comprising a bend of about 140° to 90° when more space is required for connecting the vascular system of the subject.

The coupling plate has a flat configuration with a first side and a second side, wherein the second side is shaped as a coupling surface configured to be coupled to the docking plate in a tight fit by means of the fastening means. The first and second receptors are through-holes having the same outline as the open ends of the docking portions of the first and second coupling elements. On the coupling surface side of the coupling plate, the first and second receptors are surrounded by coupling grooves arranged to receive said outwardly turned rims provided on the collars.

The docking plate is flat and has a docking surface configured to abut the coupling surface in a tight fit when the coupling plate is connected to the docking plate by fastening means.

The first and second docking ports are through-holes arranged to receive resilient docking portions provided on first and second channel connectors. The channel connectors are connected to the inlet and outlet channels of said artificial heart pump. The first and second docking ports cooperate with the inlet channel and outlet channel respectively providing the entrance and exit openings to said channels of the artificial heart pump.

On the docking surface side of the docking plate, the first and second docking ports are surrounded by docking port grooves arranged to receive rimmed flanges provided on the resilient docking portions of the first and second channel connectors. When the docking plate is fitted to the first and second channel connectors, the rimmed flanges of the resilient docking portions are flush with the docking surface of said docking plate.

When the coupling plate is connected to the docking plate, the first and second channel connectors fitted in the first and second docking ports of the docking plate are arranged to cooperate with the open ends of the resilient coupling portions fitted in the first and second receptors of the coupling plate.

The coupling plate and the docking plate are both made from a stiff bio-compatible material of the group consisting of titanium, ceramics, polytetrafluoroethylene (PTFE) coated metal, diamond coated metal, silicone or polyurethane coated metals or a combination thereof.

The vascular coupling device is provided with fastening means for fastening said coupling plate to the docking plate configured to be arranged on an artificial heart pump. The one or more fastening means may be chosen from the group consisting of screw joint reinforcements, bolts and nuts, rivets, glue, and clamps, or a combination thereof.

The docking plate further comprises an encasing sac. The encasing sac extends from the docking plate around the artificial heart pump enclosing the artificial heart pump to protect the pump from tissue ingrowth. The encasing sac serves as a pericardium of a natural heart.

The invention also relates to an artificial heart pump connected to a vascular coupling device as described above.

The invention also relates to a Total Artificial Heart (TAH) connected to a vascular coupling device as described above.

DETAILED DESCRIPTION

In the following detailed description, reference is made to the accompanying set of drawings that form a part of the description and in which several specific embodiments are shown by way of illustration. It is to be understood that other embodiments are contemplated and may be made without departing from the scope of the present invention. The following detailed description, therefore, is not to be taken in a limiting sense.

The terms "a", "an", and "the" include plural referents unless the content clearly dictates otherwise. The term "or" is generally employed in its sense including "and/or" unless the content clearly dictates otherwise FIGS. 1a-c, 2a-c and 4c all disclose vascular coupling devices 10 for connecting one or more artificial heart pumps to the vascular system of a subject.

The vascular coupling device 10 is easily connected and/or disconnected to the artificial heart pump and forms a leak-proof and safe conduit between the patient's vascular system and the artificial heart pump.

Figure 4A:
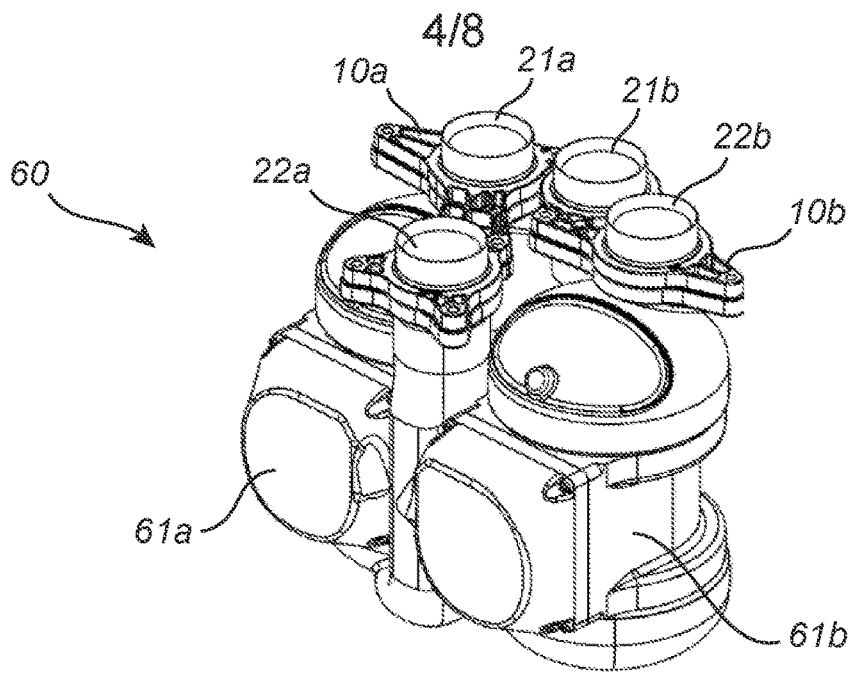
FIG. 4a discloses a vascular coupling device when connected to a total artificial heart, FIG. 4b discloses a top view of a vascular coupling device when connected to a total artificial heart
Figure 4B:
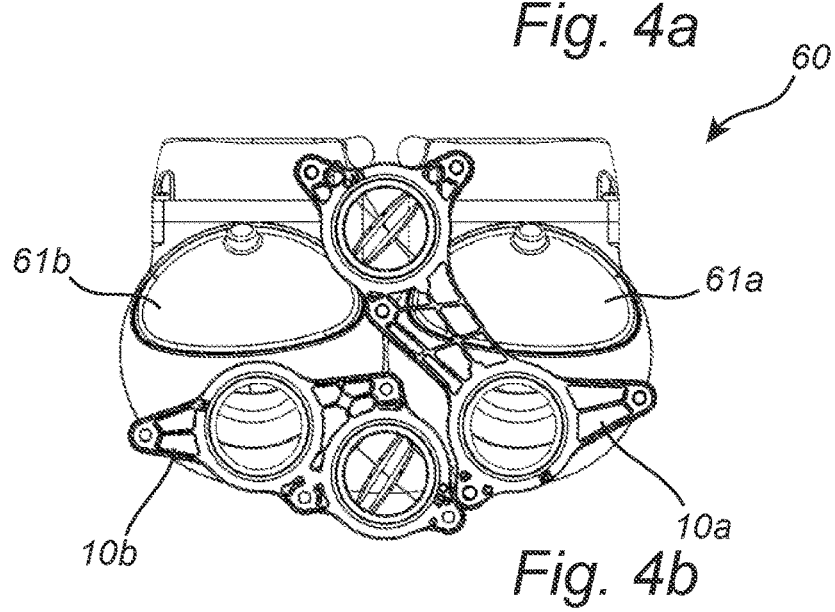
FIG. 4c is a perspective view of two differently shaped vascular coupling devices.
Figure 4C:
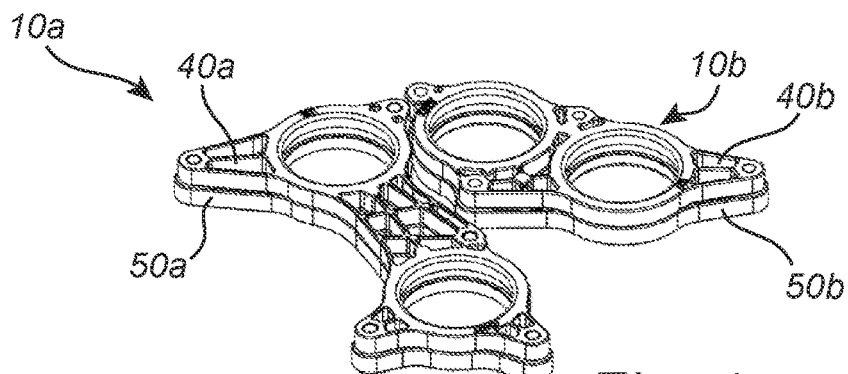

FIGS. 4a and b disclose a TAH comprising two artificial heart pumps 61a, 61b and two vascular coupling devices 10a, 10b. Two vascular coupling devices 10a, 10b are required for connecting a first heart pump 61a to the pulmonary circuit and a second heart pump 61b to the systemic circuit. As can be seen in FIGS. 4a-c, the vascular coupling devices 10a, 10b used for the different circuits may differ slightly in shape (e.g. in size) in order to accommodate the fitting to the heart pumps 61a, 61b to the vascular system of the subject as can be seen especially in FIG. 4c wherein two alternative shapes of the vascular coupling devices 10a and 10b are shown. However, the main features are the same for both vascular coupling devices 10a, 10b and the description as follows will therefore apply to both vascular coupling devices 10a, 10b regardless whether it is fitted to the pulmonary or systemic circuit of a subject.

Figure 1A:
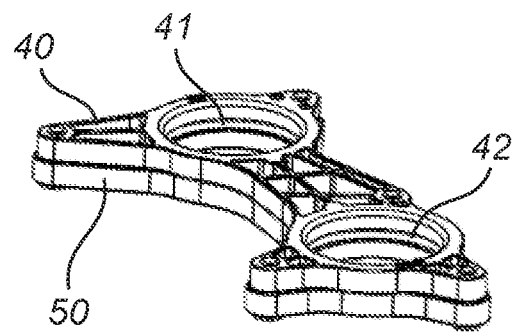
FIGS. 1a-c disclose the vascular coupling device
Figure 1B:
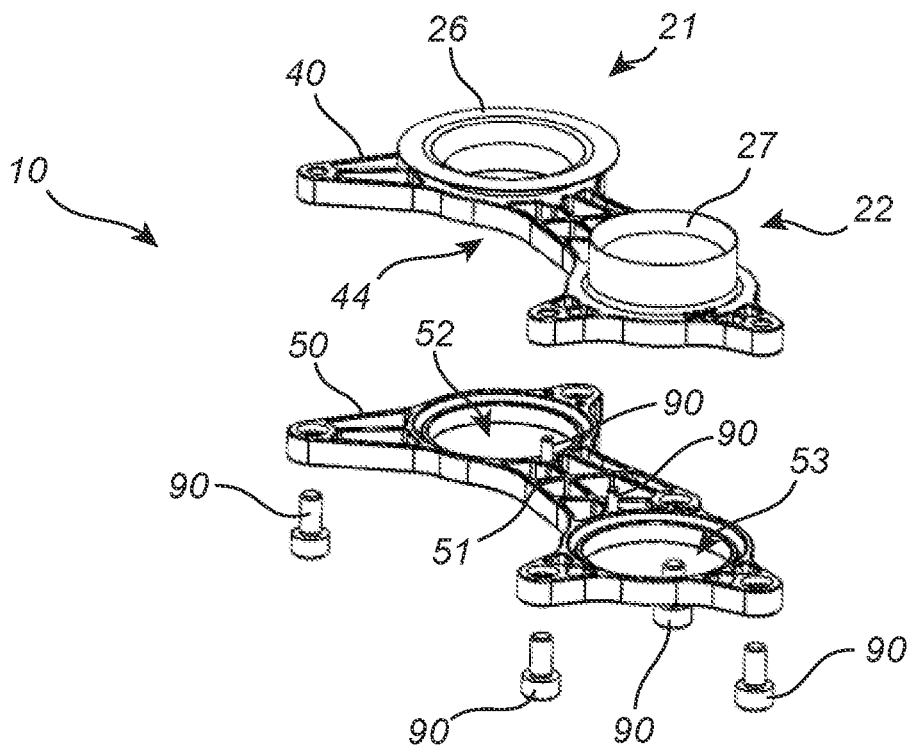
Figure 1C:
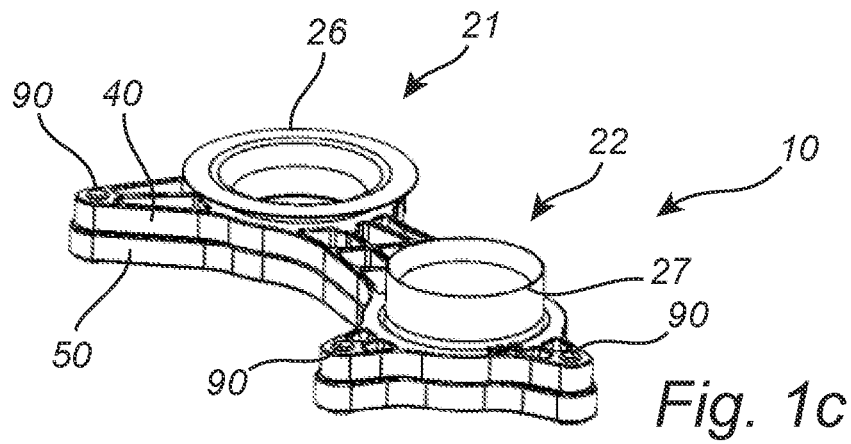

As can be seen in FIGS. 1b-c, each vascular coupling device 10 comprises a first and a second coupling element 21, 22, a coupling plate 40, a docking plate 50 and fastening means 90 for connecting the coupling plate 40 to the docking plate 50.

Figure 3A:
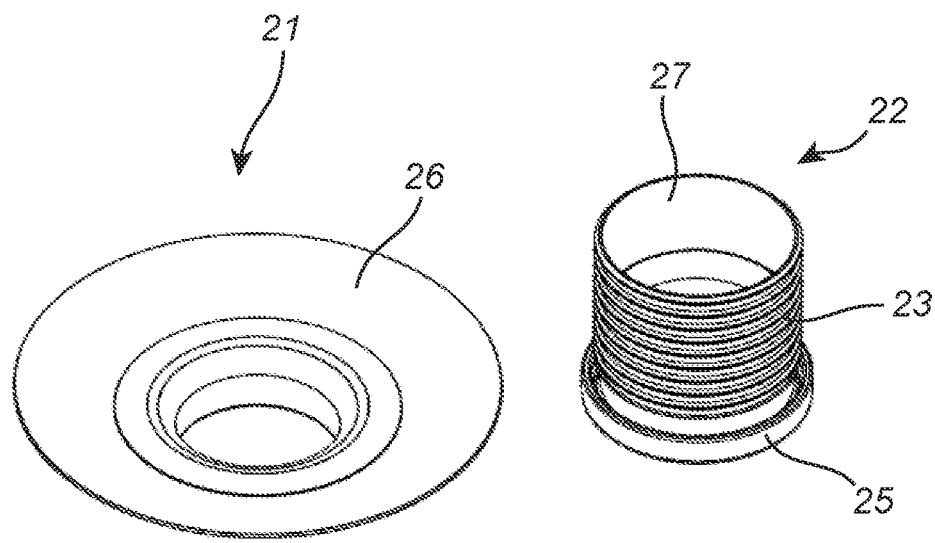
FIG. 3a discloses the first and second coupling elements of the vascular coupling device and FIG. 3b discloses cross-sectional views of said coupling elements.
Figure 3B:
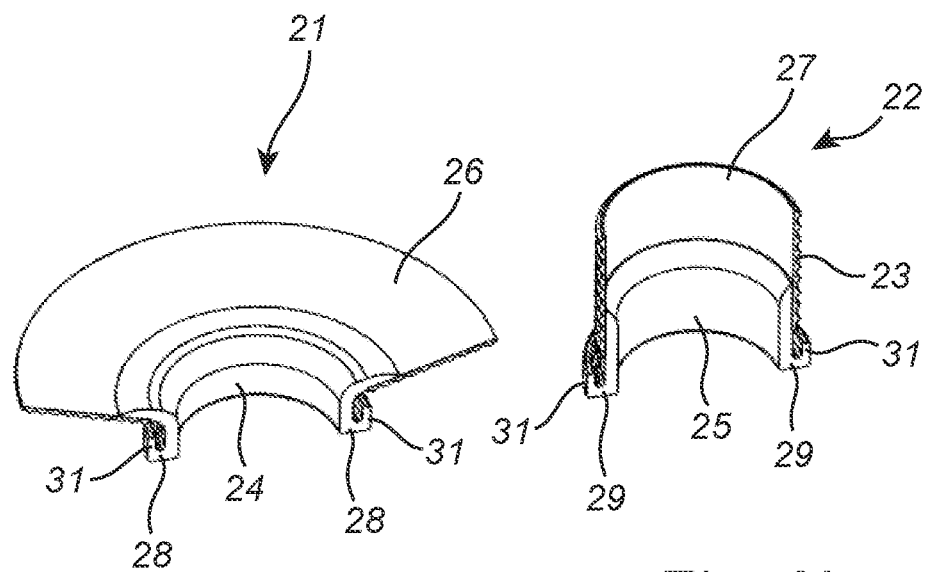

The first and second coupling elements 21, 22 each have a tubular configuration with a first end comprising a coupling portion 24, 25 made from a resilient material, and a second end comprising vascular grafting material 26, 27 (see FIGS. 3a-b).

When used herein the term "resilient material" is intended to mean a material having the ability to withstand elastic deformation without deforming plastically. The resilient coupling portions 24, 25 must be bio-compatible and may be chosen from resilient materials of the group consisting of polyethylene, polyamide, polymethylmethacrylate, polytetrafluoroethylene, polyurethane, and silicones such as dimethyl siloxane, polydimethylsiloxane, and decamethyl cyclopentasiloxane, or combinations thereof.

The resilient coupling portions 24, 25 each have an open end. Said open ends may have any geometric outline such as circular, oval, quadratic or rectangular. In the embodiment shown in FIGS. 3a-b the open ends are circular. The outer circumferences of the open ends are provided collars 28, 29 with outwardly folded rims 31.

The vascular system of the subject is grafted onto the vascular grafting material 26, 27 arranged at the second ends of the first and second coupling elements 21, 22 (see FIGS. 3a-b). The vascular grafting material 26, 27 must be blood compatible and is chosen from the group comprising any known commercially available vascular grafting materials such as e.g. polyethylene teraphthalate (Dacron), expanded polytetrafluoroethylene (ePTFE), Polyamide (nylon) and polyurethane. In one embodiment the vascular grafting material is polyethylene teraphthalate (Dacron).

A tubular midsection 23 connects said first and second ends of the coupling elements 21, 22. Advantageously the tubular midsection 23 (as best viewed in FIGS. 3a-b) is made from the same bio-compatible and blood compatible material as used for the vascular grafting material 26, 27. The tubular midsection 23 may have different shapes depending on whether the coupling element 21, 22 is connected to the pulmonary or the systemic circuit of the subject. The shape of the tubular midsection 23 is designed to cause the least possible strain on the graft connection between arteries/veins and the vascular grafting material 26, 27 of the first and second coupling elements 21, 22. The tubular midsection 23 is normally straight as seen in FIGS. 1-5, but may also have the shape of a tube comprising a bend of about 140° to 90° when more space is required for connecting the vascular system of the subject (see FIG. 8).

The coupling plate 40 comprises a first receptor 41 and a second receptor 42 for receiving the first and second coupling elements 21, 22 respectively. The first and second receptors 41, 42 are through-holes having the same outline as the open ends of the resilient coupling portions 24, 25 of the coupling elements 21, 22 (see FIGS. 1a-c and 2a-c). The coupling plate 40 has a first and a second side. The second side is shaped as a coupling surface 44 configured to abut a docking surface 51 of the docking plate 50.

The resilient coupling portions 24, 25 of the coupling elements 21, 22 are arranged to fit into the through-holes of the receptors 41, 42 of the coupling plate 40. The fitting of the coupling elements 21, 22 into the coupling receptors 41, 42 is done by squeezing the resilient coupling portions 24, 25 slightly and pushing the open ends provided with collars 38, 29 through the through-holes of the coupling receptors 41, 42 from the first side to the second side with the coupling surface 44 of the coupling plate 40. Grooves 45, 46 are provided around the circumferences of the receptor 41, 42 through-holes on the coupling surface 44 of the coupling plate 40 (see cross-sectional views of vascular coupling device 10 in FIGS. 2a-c). The grooves 45, 46 are configured to receive outwardly folded rims 31 arranged on the collars 28, 29 of the resilient coupling portions 24, 25 such that the outwardly turned rims 31 rest inside the grooves 45, 46 and the second ends of the coupling elements 21, 22 provided with vascular grafting material 26, 27 protrude through the coupling receptors 41, 42 on the first side of the coupling element 40 (see FIGS. 2b and c). When the resilient coupling portions 24, 25 are fitted inside the coupling receptors 41, 42, the coupling collars 28, 29 will be flush with the coupling surface 44 of the coupling plate 40 forming a substantially flat coupling surface 44 that will abut the docking plate 50 in a leak-free manner (see FIG. 2c).

The coupling plate 40 further comprises one or more fastening means 90 for connecting said coupling plate 40 to the docking plate 50.

The docking plate 50 is flat with a first side and a second side, said second side forming a docking surface 51 configured to abut said coupling surface 44 of the coupling plate 40 when the coupling plate 40 and the docking plate 50 are connected together.

Figure 5A:
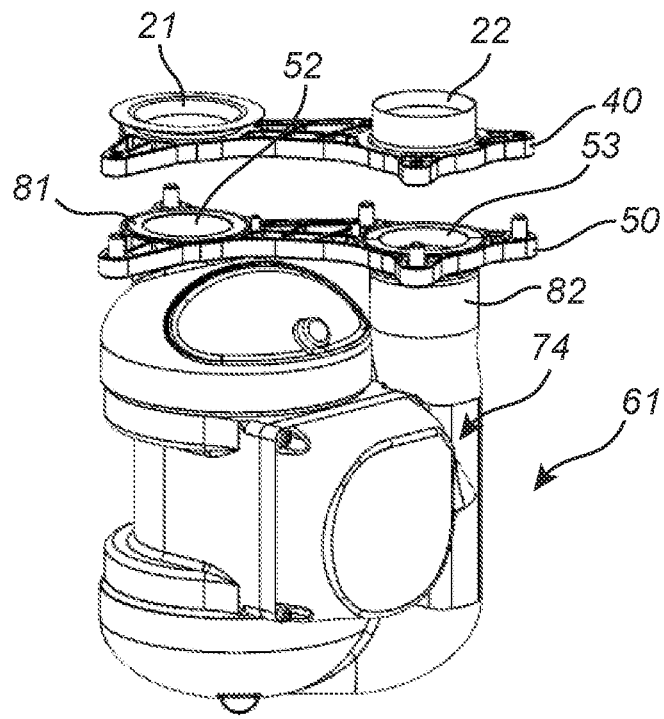
FIG. 5a is a view of a vascular coupling device connected to an artificial heart pump and FIG. 5b is a cross-sectional view of said connection.
Figure 5B:
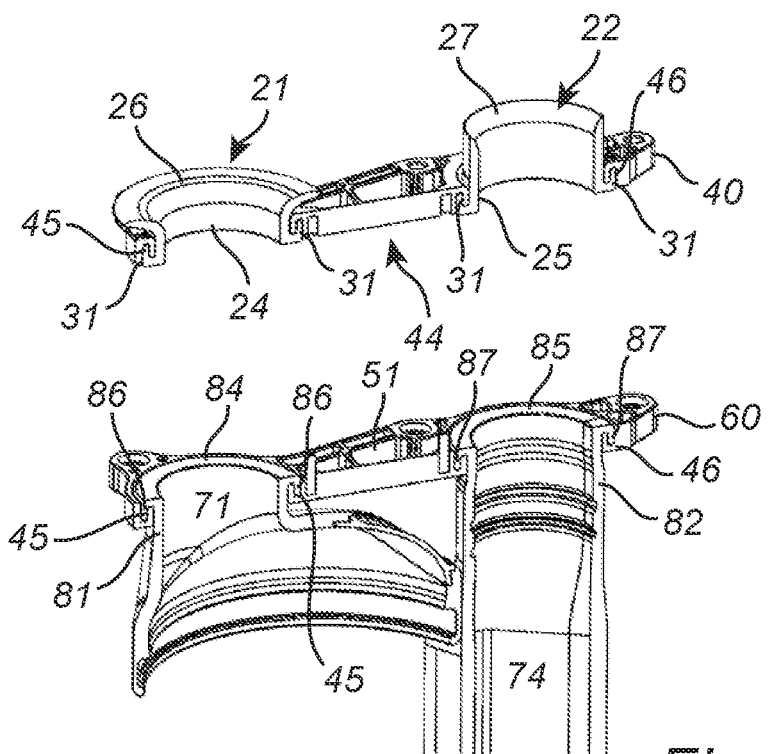

The docking plate 50 is configured to be arranged to the artificial heart pump 61 of a total artificial heart 60 (see FIGS. 5a-b). The docking plate 50 comprises a first docking port 52 and a second docking port 53. Said first and second docking ports 52, 53 are formed by through-holes in the docking plate 50 (see FIGS. 1b and 2a). The first docking port 52 cooperates with an inlet channel 71 and the second docking port 53 cooperates with an outlet channel 74 of the artificial heart pump 61 in a TAH 60 (see FIGS. 5a and b). The first and second docking ports 52, 53 provide the entrance and exit openings to said channels 71, 74 respectively of the artificial heart pump 61. In one embodiment the docking plate 50 with the first and second docking ports 52, 53 is permanently fixed to the inlet and outlet channels 71, 74 of the artificial heart pump 61 (not shown). However, in one advantageous embodiment the inlet and outlet channels 71, 74 of the artificial heart pump 61 are fitted with resilient channel connectors 81, 82 configured to connect to said first and second docking ports 52, 53 (see FIGS. 5a-b, and 6) in a similar manner as described for the coupling elements 21, 22 and the coupling plate 40 above.

The resilient channel connectors 80, 81 are tubular shaped with a first end connected to the inlet/outlet channels 71, 74, of the artificial heart pump 61 and a second end with an opening provided with a resilient docking portion 84, 85 shaped as an outwardly projecting rimmed flange 86, 87. The outwardly folded rimmed flanges 86, 87 are configured to cooperate with docking port grooves 54, 55 surrounding the docking port through holes on the docking surface 51 of the docking plate 50 (see FIGS. 2b-c and 5b).

Figure 2A:
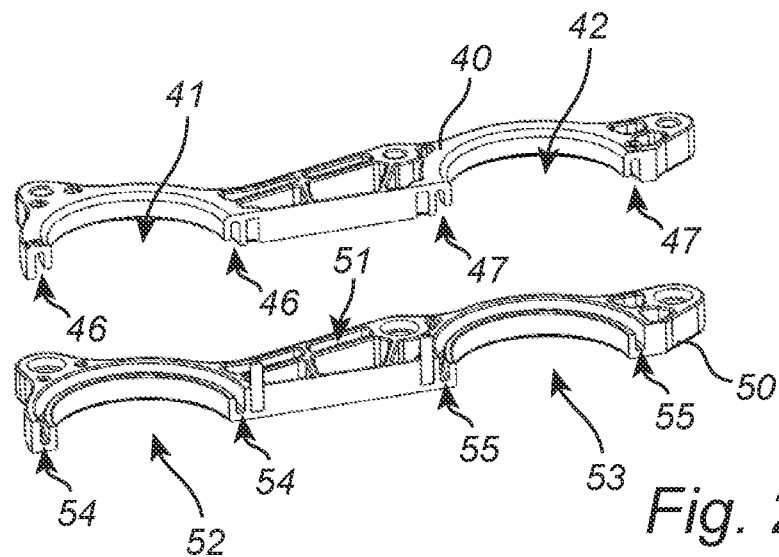
FIG. 2a-c disclose cross-sectional views of the vascular coupling device
Figure 2B:
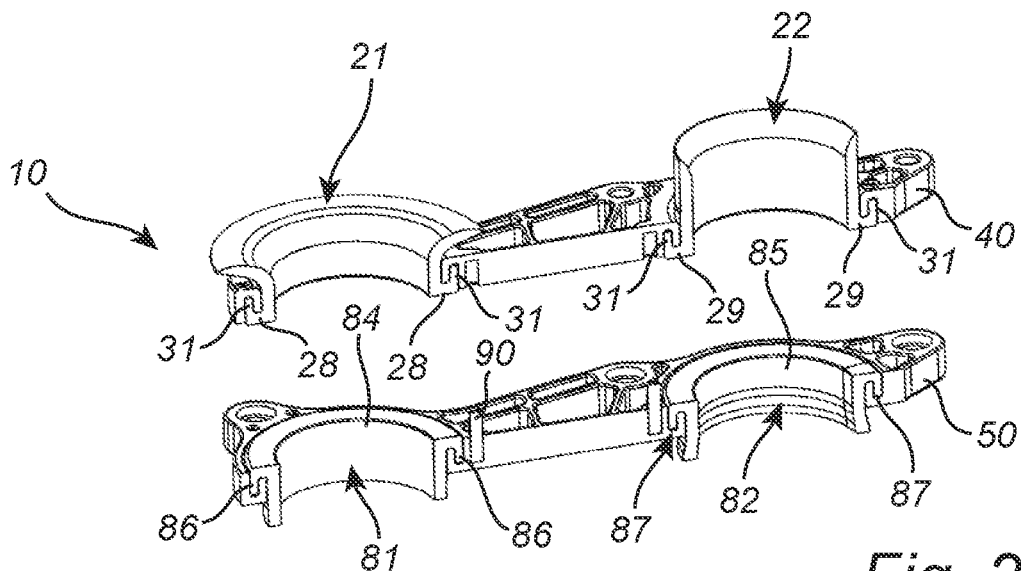
Figure 2C:
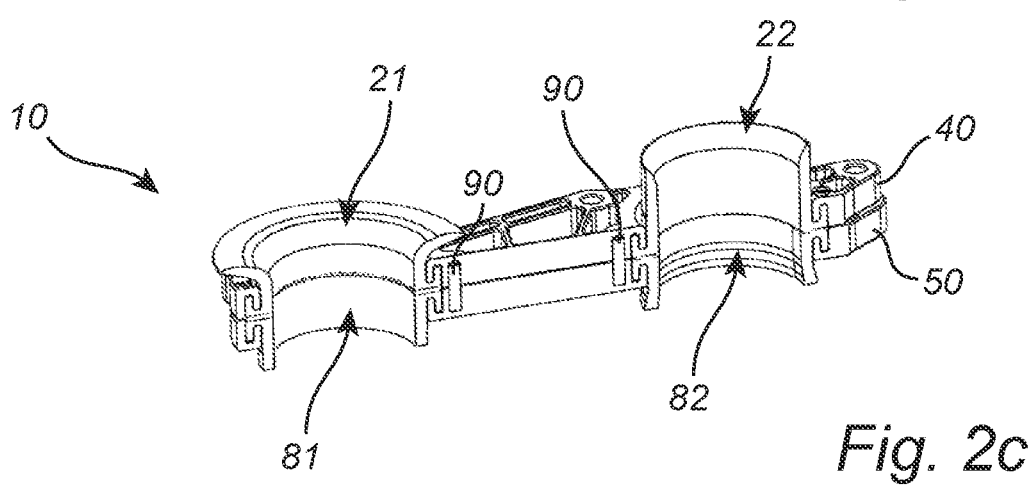

In order to connect the channel connectors 80, 81 to the docking ports 52, 53, the resilient docking portions 84, 85 of the channel connectors 80, 81 are carefully squeezed and pushed through the through-holes of the docking ports 52, 53 such that the outwardly folded rims 86, 87 of the resilient docking portions 84, 85 can be fitted inside the grooves 54, 55 surrounding the docking port through-holes 52, 53 (see FIGS. 2b-c). When the channel connectors 81, 82 are fitted inside the docking ports 52, 54 the resilient docking portions 84, 85 will be flush with the docking surface 51 of the docking plate 50 forming a substantially flat surface that will abut the coupling surface 44 of the coupling plate 40 in a leak-free manner (FIGS. 2b and 5b).

The coupling plate 40 and the docking plate 50 are made from a stiff bio-compatible material of the group consisting of titanium, ceramics, polytetrafluoroethylene (PTFE) coated metal, diamond coated metal, silicone or polyurethane coated metals or a combination thereof.

Figure 6:
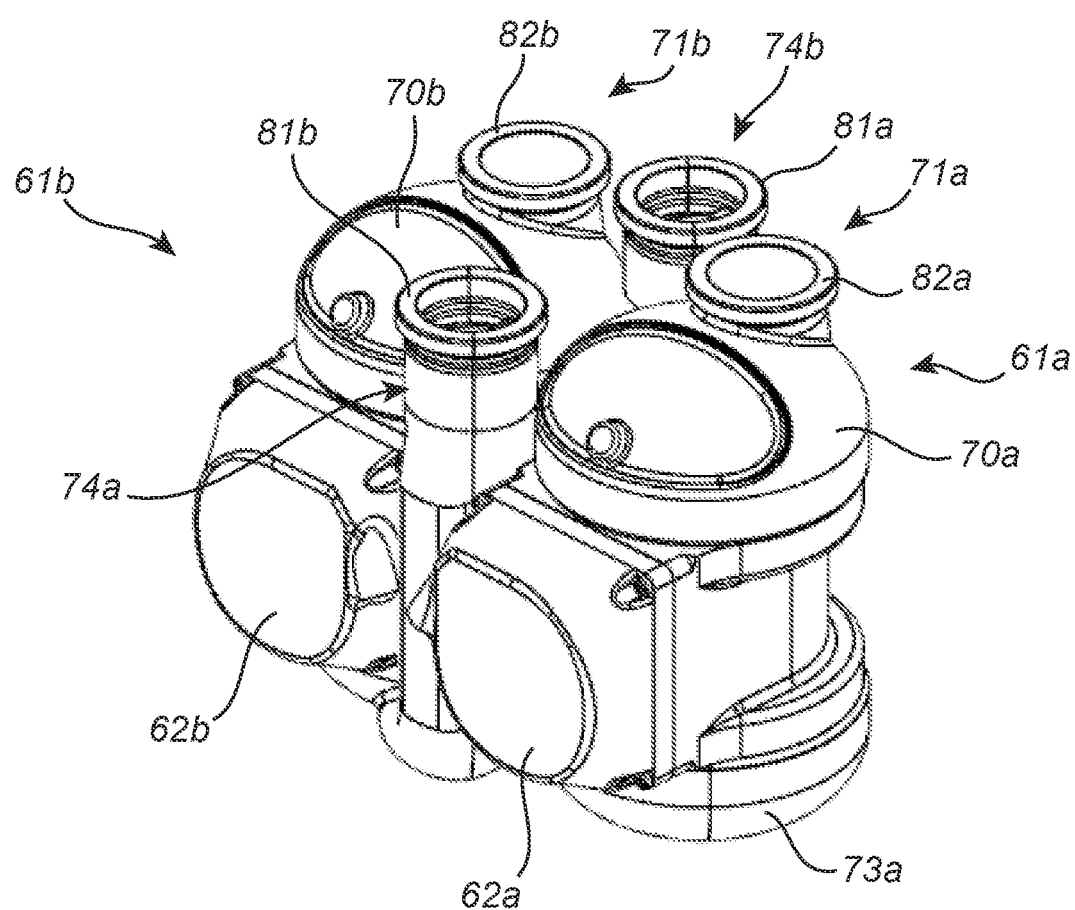
FIG. 6 is a view of the total artificial heart fitted with channel connectors.

The total artificial heart 60 comprises a first and a second artificial heart pump 61a, 61b and first and second pump actuation means 62a, 62b enclosed in a blood pump housing device (see FIG. 6). The first and second artificial heart pumps 61a, 61b are substantially identical and correspond to the left and right side of a natural heart respectively.

The first and second pump actuation means 62a, 62b actuate movement of the first and second artificial heart pumps 61a, 61b to induce a blood flow in a body's vascular system such that blood flows through the separate pulmonary and systemic circuits of a subject.

The pulmonary circuit carries carbon dioxide-rich blood from the TAH 60 to the gas-exchange surfaces of the lungs of the subject and returns oxygen-rich blood to the TAH 60; and the systemic circuit transports oxygen-rich blood from the TAH 60 to the rest of the body's cells of the subject, returning carbon dioxide rich blood back to the TAH 60.

Figure 7:
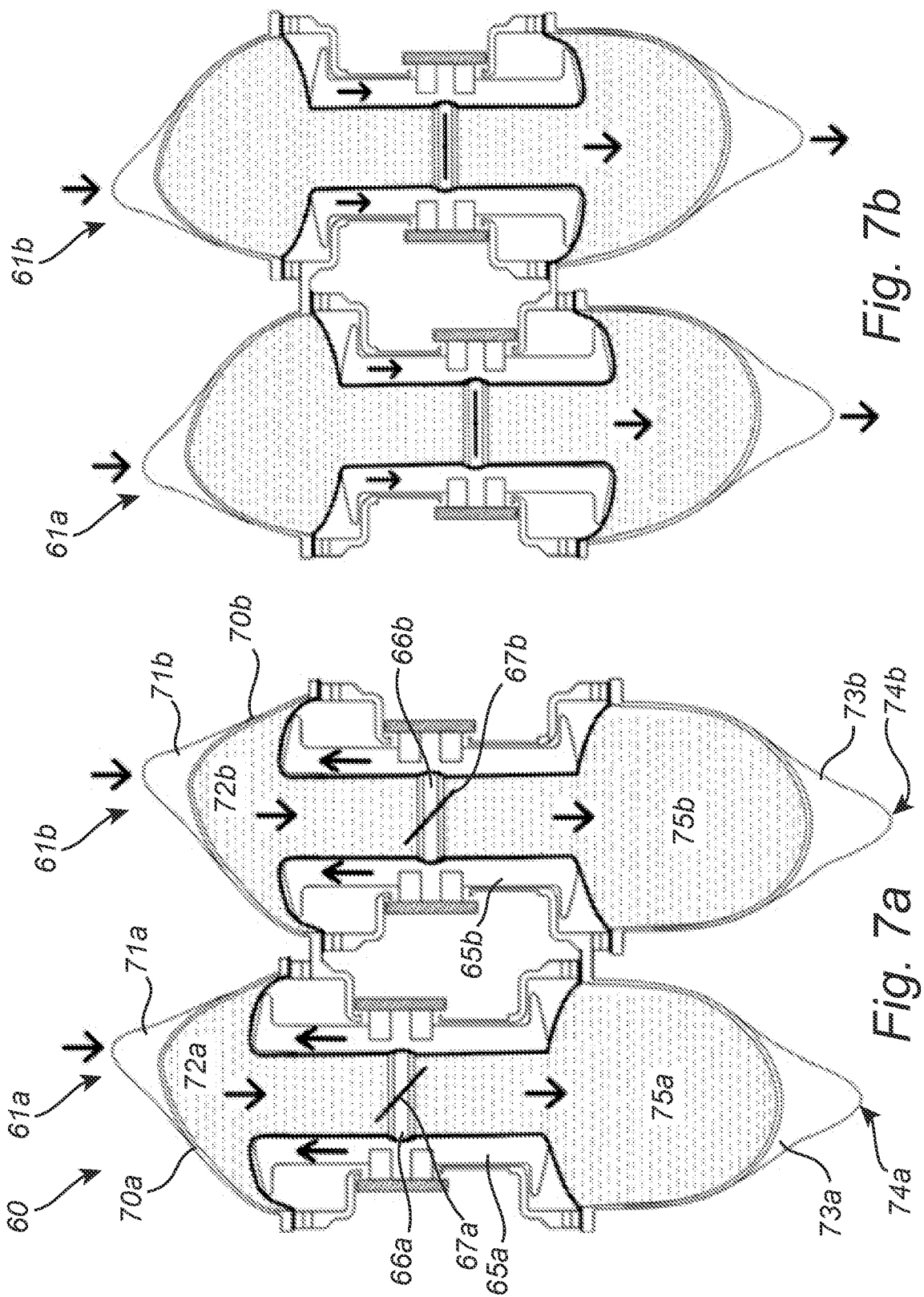
FIGS. 7a and b disclose the pumping action of the total artificial heart

The blood pump housing device 63 comprises two artificial heart pump receiving parts 64a, 64b, each of which encloses a valve cylinder 65a, 65b (FIG. 7a) movably arranged inside said pump receiving part 64a, 64b. Each valve cylinder 65a, 65b is separated by valve planes 66a, 66b, provided with valves 67a, 67b such that the valve planes 64a, 64b divide the valve cylinders 65a, 65b into two parts, one upper part and one lower part (FIG. 7a). The first and second artificial heart pumps 61a, 61b are substantially mirror images of each other and mimic a natural heart of a human, and the valves 66a, 66b provided in the valve cylinders 65a, 65b of each artificial heart pump 61a, 61b, correspond to the mitral valve 66a on the left side of the natural heart (i.e. in the first artificial heart pump) and the tricuspid valve 66b on the right side (i.e. in the second artificial heart pump).

Each pump receiving part 64a, 64b has an upper open end and a lower open end. The upper open ends of the pump receiving parts are fitted with upper covers 70a, 70b, each of which is provided with an inlet channel 71a, 71b. The upper covers 70a, 70b together with the upper parts of the valve cylinders 65a 65b form artificial atriums 72a, 72b corresponding to the atriums of the natural heart (see FIG. 7a). The upper cover 70a of the first artificial heart pump 61a comprises the first inlet channel 71a of the TAH 60 and the upper cover 70b of the second artificial heart pump 61b comprises the second inlet channel 71b of the TAH 60.

The lower open ends of the pump receiving parts are fitted with lower covers 73a, 73b, each of which is provided with an outlet channel 74a, 74b. The lower covers 73a, 73b together with the lower parts of the valve cylinders 65a, 65b form artificial ventricles 75a, 75b corresponding to the ventricles of the natural heart. The lower cover 73a, of the first artificial heart pump 61a comprises the first outlet channel 74a of the TAH 60 and the lower cover 73b of the second artificial heart pump 61b comprises the second outlet channel 74b of the TAH 60.

Pump actuating means 62a, 62b, are configured to apply a movement to said valve cylinders 65a, 65b in an upward and downward direction in response to control signals from a control unit (not shown) such that when the valve cylinders 65a, 65b move in an upward direction inside the blood pump housing device (see FIG. 7a), the valves 67a, 67b provided in the valve planes 66a, 66b are in an open position allowing a flow of blood from the artificial atrium 72a, 72b to the artificial ventricle 75a, 75b, and when the valve cylinders 65a, 65b move in a downward direction (see FIG. 7b) the valves 67a, 67b are in the closed position and blood is ejected from the artificial ventricles 75a, 75b through the outlet channels 74a, 74b.

In the TAH 60, the artificial atrium 72b of the second artificial heart pump 61b (corresponding to the right atrium of a natural heart) receives carbon dioxide-rich blood from the systemic circuit, and the artificial ventricle 75b of the second artificial heart pump 61b (corresponding to the right ventricle of a natural heart) discharges the carbon dioxide-rich blood into the pulmonary circuit of the subject. The artificial atrium 72a of the first artificial heart pump 61a (corresponding to the left atrium of a natural heart) receives oxygen-rich blood from the pulmonary circuit and the artificial ventricle 75a of the first artificial pump 61a (corresponding to the left ventricle of a natural heart) ejects the oxygen-rich blood into the systemic circuit of the subject.

The first and second outlet channels 74a, 74b of each artificial heart pump 61a, 61b of the TAH 60 are provided with one-way outlet valves 76a, 76b to prevent the return of blood back into the artificial ventricles 75a, 75b after the blood has been ejected through the outlet channels 74a, 74b. The one-way outlet channel valves 76a, 76b correspond to the aortic valve or the pulmonary valve respectively of the natural heart.

As described above, the first and second docking ports 52, 53 provide the exit and entrance openings for the inlet 71 and outlet 74 channels respectively of the artificial heart pump 61. When the coupling plate 40 is connected to the docking plate 50 by means of the fastening means 90, the first and second channel connectors 80, 81 arranged inside the first and second docking ports 52, 53 are adopted to cooperate with the open ends of the first and second coupling elements 21, 22 fitted in the first and second receptors 41, 42 of the coupling plate 40, thereby forming a conduit between the subject's vascular system and the artificial heart pump 61 through which blood is transported back and forth (see FIG. 2c). When the vascular system of the subject is connected to two artificial heart pumps 61a, 61b of a TAH 60 the vascular devices 10a, 10b form a safe conduit between the TAH 60 and the systemic and pulmonary systems of the subject (not shown).

A method for connecting a TAH 60 to a subject will now be described. Two vascular coupling devices 10a, 10b are required to connect the TAH 60 to a subject (see FIGS. 4a-c). The docking plates 50a, 50b of the first and second vascular coupling devices 10a, 10b are connected to the inlet and outlet channels 71a, 71b, 74a, 74b of the artificial pumps 61a, 61b before the procedure of connecting the TAH to the vascular circuit of the patient is started (see FIGS. 5a and b). The procedure for coupling of a docking plate 50, to an artificial heart pump 61 is as follows:

The inlet and outlet channels 71, 74 of the artificial heart pump 61 are advantageously already provided with first and second channel connectors 81, 82 (see FIGS. 5a and b). The docking plate 50 is thereafter connected to the first and second channel connectors 81, 82 by gently squeezing the resilient docking portions 84, 85 of the channel connectors 81, 82 and pushing the flanges provided with outwardly folded rims 86, 87 through the through-holes of the docking ports 52, 52 such that the outwardly folded rims 86, 87 rest inside the docking port grooves 54, 55 on the docking surface 51 of the docking plate 50 (see FIG. 2b).

Advantageously also the coupling elements 21, 22 are connected to the coupling plates 40 before the surgical procedure to remove the natural heart is started. The coupling elements 21, 22 are fitted into the receptors 41, 42 by gently squeezing the resilient coupling portions 24, 25 and pushing the open ends provided with collars 28, 29 through the receptor through-holes 41, 42 from the first side to the second side of the coupling plate 40. The outwardly folded rims 31 of the coupling collars 28, 29 are received into the coupling grooves 45, 46 on the coupling surface 44 of the coupling element 40 (see FIG. 2b).

When the resilient coupling portions 24, 25 of the first and second coupling elements 21, 22 are properly fitted in the first and second receptors 41, 42, a flat coupling surface 44 is formed on the second side of the coupling plate 40 (see FIG. 2b). Said coupling surface 44 is configured to abut the docking surface 51 of the docking plate 50 such that the open ends of the resilient coupling portions 24, 25 coincide and cooperate with the first and second docking ports 52, 53 of the docking plate 50 (see FIG. 2c).

When the TAH have been provided with the docking plates 50a, 50b and the coupling plates 40a, 40b have been fitted with the coupling elements 21, 22, the actual procedure of connecting the vascular circuit of a subject to a TAH 60 starts by removing the natural heart of the subject except for the pulmonary trunk, the aortic arch and major parts of the left and right atria.

The remains of the left atrium from the subject are grafted onto the vascular grafting material 26a of the first coupling element 21a in the first vascular coupling device 10a. Oxygenated blood from the lungs is transported through the remaining atrium into the first artificial atrium 72a (corresponding to the left atrium of a natural heart) of the first artificial heart pump 61a of the TAH 60. Blood flows from the artificial atrium 72a through the valve 67a in the valve plane 66a (corresponding to the left atrioventricular valve of a natural heart) and into the artificial ventricle 75a of the first artificial heart pump 61a when the valve cylinder 65a moves in an upwards direction.

When the valve cylinder 65a moves in a downward direction, the valve 67a in the valve plane 66a closes and blood collected in the artificial ventricle 75a of the first artificial blood pump 61a is ejected from the artificial ventricle 75a into the outlet channel 74a. The blood passes the outlet one-way valve 76a (corresponding to the aortic valve in a natural heart) and continues into the aortic arch of the subject which is grafted onto the vascular grafting material 27a on the second coupling element 22a of the first vascular coupling device 10a. The oxygenated blood now enters the systemic circuit of the subject.

Carbon dioxide rich blood returns from the systemic circuit through the remains of the right atrium from the subject which is grafted onto the vascular grafting material 26b of the first coupling element 21b of the second vascular coupling device 10b. The blood enters the second artificial atrium 72b of the second artificial heart pump 61b (corresponding to the right atrium of a natural heart). Thereafter, blood flows from the artificial atrium 72b through the valve 66b in the valve plane 67b (corresponding to the right atrioventricular valve of a natural heart) and into the second artificial ventricle 75b of the second blood pump 61b when the valve cylinder 65b moves in an upwards direction.

When the valve cylinder 65b moves in a downward direction, the valve 66b in the valve plane 67b closes and blood in the second artificial ventricle 75b is ejected from the artificial ventricle 75b into the outlet channel 74b. The blood passes the outlet one-way valve 76b (corresponding to the pulmonary valve in a natural heart) and continues into the pulmonary trunk of the subject which has been grafted onto the vascular grafting material 27b of the second coupling element 22b in the second vascular coupling device 10b. The carbon dioxide-rich blood now enters the pulmonary circuit of the subject to become re-oxygenated in the lungs and the oxygenated blood is again transported through the remaining atrium into the first artificial atrium 72a.

Figure 8:
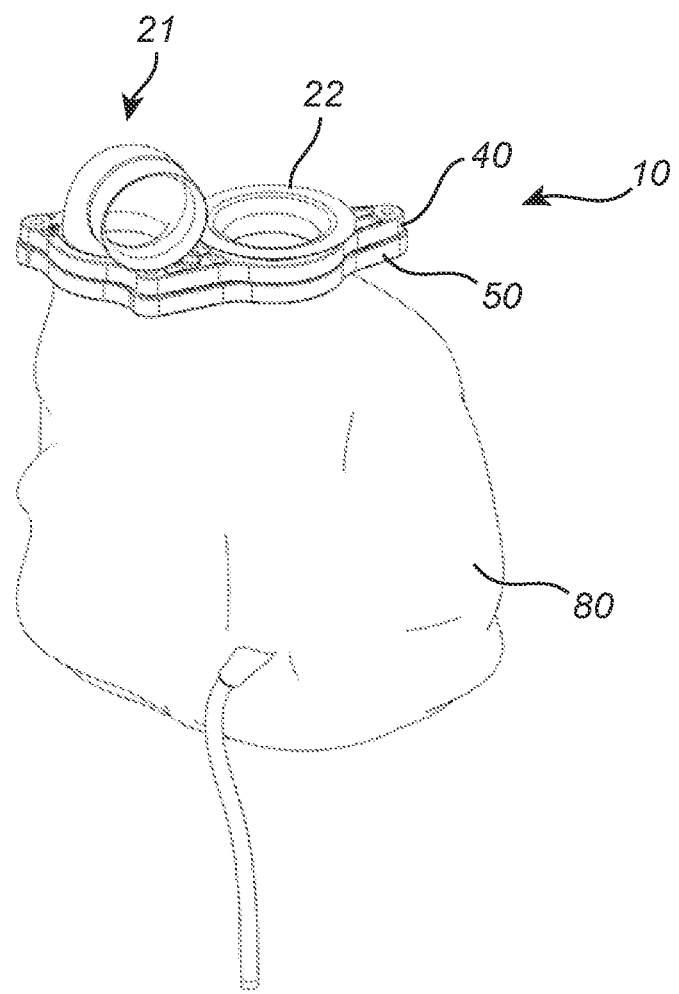
FIG. 8 is a view of the vascular coupling device connected to an enclosing sac.

An encasing sac 80 is attached to the docking plate 50 arranged on the artificial heat pump 61 (FIG. 8). The encasing sac 80 receives and encloses the artificial heart pump 61 to protect the pump from tissue ingrowth.

The invention claimed is:

1. A vascular coupling device for connecting an artificial heart pump to a vascular circuit of a subject, said vascular coupling device comprising:
   a first and a second coupling element, each one of said first and second coupling elements has a first end comprising a resilient coupling portion a second end comprising a vascular grafting material, and a tubular midsection is arranged between said first and second ends; and
   a coupling plate comprising a first receptor and a second receptor configured and adapted for receiving said resilient coupling portions of the first and second coupling elements; and
   a first channel connector configured to be arranged to an inlet channel of said artificial heart pump and a second channel connector configured to be arranged to an outlet channel of said artificial heart pump, each one of said first and second channel connectors comprising a resilient docking portion, each resilient docking portion having substantially a same tubular shape as each channel connector; and
   a docking plate, comprising a first and a second docking port configured for receiving the resilient docking portions of the first and second channel connectors; and
   one or more fastening means for connecting said coupling plate to the docking plate, wherein when said coupling plate is connected to said docking plate said first and second channel connectors fitted in said first and second docking ports of the docking plate are arranged to cooperate with said open ends of the resilient coupling portions fitted in said first and second receptors of said coupling plate.

2. The vascular coupling device according to claim 1, wherein said resilient coupling portions have open ends with circular outlines.

3. The vascular coupling device according to claim 2, wherein said open ends are provided with collars with outwardly folded rims.

4. The vascular coupling device according to claim 1, wherein said tubular midsection comprises a bend of 140° to 90°.

5. The vascular coupling device according to claim 1, wherein said tubular midsection is straight.

6. The vascular coupling device according to claim 1, wherein the coupling plate is flat with a first side and a second side, wherein said second side is a docking surface configured to be coupled to the docking plate in a tight fit by means of the fastening means.

7. The vascular coupling device according to claim 6, wherein on said coupling surface said first and second receptors are surrounded by coupling grooves arranged to receive said outwardly turned rims of said collars.

8. The vascular coupling device according to claim 1, wherein the first and second receptors are through-holes having the same outline as the open ends of the resilient coupling portions of the first and second coupling elements.

9. The vascular coupling device according to claim 1, wherein said docking plate is flat and has a docking surface configured to abut said coupling surface in a tight fit when said coupling plate is connected to said docking plate by said fastening means.

10. The vascular coupling device according to claim 9, wherein on said docking surface said first and second docking ports are surrounded by docking port grooves arranged to receive rimmed flanges provided on said resilient docking portions of said first and second channel connectors.

11. The vascular coupling device according to any claim 1, wherein said coupling plate and said docking plate are made from a stiff material.

12. The vascular coupling device according to claim 11, wherein said stiff material is stainless steel, titan, polyurethane.

13. The vascular coupling device according to claim 1, wherein said docking plate comprises an encasing sac.

14. An artificial heart pump connected to a vascular coupling device according to claim 1.

15. A Total Artificial Heart connected to a vascular coupling device according to claim 1.

* * * * *